US007184833B2

(12) United States Patent
Ganion et al.

(10) Patent No.: US 7,184,833 B2
(45) Date of Patent: Feb. 27, 2007

(54) MULTIPLE PACING OUTPUT CHANNELS

(75) Inventors: Vincent P. Ganion, Andover, MN (US);
Glenn C. Zillmer, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 475 days.

(21) Appl. No.: 10/680,695

(22) Filed: Oct. 7, 2003

(65) Prior Publication Data

US 2005/0075677 A1 Apr. 7, 2005

(51) Int. Cl.
*A61N 1/00* (2006.01)
*A61B 5/04* (2006.01)

(52) U.S. Cl. .................. 607/9; 607/5; 607/13; 600/509
(58) Field of Classification Search ...................... 607/9
See application file for complete search history.

(56) References Cited

U.S. PATENT DOCUMENTS

| 4,343,312 | A | | 8/1982 | Cals et al. | |
|---|---|---|---|---|---|
| 4,373,531 | A | | 2/1983 | Wittkampf et al. | |
| 4,821,724 | A | | 4/1989 | Whigham et al. | |
| 4,903,700 | A | | 2/1990 | Whigham et al. | |
| 5,213,098 | A | * | 5/1993 | Bennett et al. | 607/18 |
| 5,755,742 | A | * | 5/1998 | Schuelke et al. | 607/27 |
| 6,298,267 | B1 | * | 10/2001 | Rosborough et al. | 607/6 |
| 6,438,408 | B1 | * | 8/2002 | Mulligan et al. | 600/510 |
| 6,469,554 | B1 | | 10/2002 | Harpham | |
| 6,472,926 | B2 | | 10/2002 | Taito et al. | |
| 2002/0049477 | A1 | * | 4/2002 | Zhang et al. | 607/9 |

FOREIGN PATENT DOCUMENTS

EP   0862484 B1   1/2003

* cited by examiner

*Primary Examiner*—George Manuel
*Assistant Examiner*—Christopher A. Flory
(74) *Attorney, Agent, or Firm*—Girma Wolde-Michael; Paul H. McDowall

(57) ABSTRACT

An implantable medical device includes two or more pacing output channels coupled to a single unipolar electrode or bipolar electrode pair. The implantable medical device can control each pacing output channel to deliver pacing pulses via the single electrode or electrode pair at different times and with different amplitudes. In some embodiments, the implantable medical device is used to deliver extra-systolic stimulation therapy. In such embodiments, a first pacing output channel can be controlled to deliver pacing pulses via the electrode or electrode pair with an amplitude sufficient to depolarize a chamber of the heart. A second pacing output channel is controlled to deliver extra-systolic pulses, which can have a lower amplitude than the pacing pulses, via the electrode or electrode pair an extra-systolic interval after sensed or paced depolarizations of the chamber. In some embodiments, the implantable medical device delivers ESS therapy and cardiac resynchronization therapy (CRT).

16 Claims, 13 Drawing Sheets

MULTIPLE PACING OUTPUT CHANNELS

CROSS REFERENCE TO RELATED APPLICATIONS

The present patent application hereby cross-references and incorporates by reference the entire contents of the following applications, each of which is filed on even date herewith: non-provisional U.S. application Ser. No. 10/680,528 entitled, "REFRACTORY PERIOD TRACKING AND ARRHYTHMIA DETECTION," non-provisional U.S. application Ser. No. 10/680,462 entitled, "METHOD AND APPARATUS FOR CONTROLLING EXTRA-SYSTOLIC STIMULATION (ESS) THERAPY USING ISCHEMIA DETECTION," non-provisional U.S. application Ser. No. 10/680,494 entitled, "METHOD AND APPARATUS FOR OPTIMIZATION AND ASSESSMENT OF RESPONSE TO EXTRA-SYSTOLIC STIMULATION (ESS) THERAPY," non-provisional U.S. application Ser. No. 10/680,493 entitled, "EXTRA-SYSTOLIC STIMULATION THERAPY DELIVERY AND SENSING VIA DIFFERENT ELECTRODE SETS," non-provisional U.S. application Ser. No. 10/692,990 entitled, "CARDIAC PACING MODALITY HAVING IMPROVED BLANKING, TIMING, AND THERAPY DELIVERY METHODS FOR EXTRA-SYSTOLIC STIMULATION PACING THERAPY," and non-provisional U.S. application Ser. No. 10/703,956 entitled, "SECURE AND EFFICACIOUS THERAPY DELIVERY FOR AN EXTRA-SYSTOLIC STIMULATION PACING ENGINE."

TECHNICAL FIELD

The invention relates to implantable medical devices, and more particularly, to implantable medical devices for cardiac pacing.

BACKGROUND

Decades ago so-called paired- or coupled-pacing was used, primarily in the context of experiments and studies. This type of pacing involves the delivery of an extra-systolic stimulus (ESS), in effect a pacing-level pulse of electricity, to a chamber of the heart a relatively short interval after a paced or intrinsic depolarization of that chamber. The ESS pulse is applied following the refractory period after an initial paced or spontaneous depolarization, and results in a second electrical depolarization of the chamber substantially free of an attendant myocardial contraction. The second depolarization of the chamber effectively prolongs the refractory period after the mechanical contraction of the chamber caused by the first paced or intrinsic depolarization.

The prolonged refractory period caused by ESS therapy delivery effectively slows the heart rate from its spontaneous rhythm. Consequently, the prolonged refractory period allows a greater time for filling of the chamber. Further, ESS therapy delivery causes an augmentation of contractile force of the chamber following the cardiac cycle during which an ESS pulse was applied. If no additional ESS pulses are applied in subsequent cardiac cycles the magnitude of the augmentation attenuates over the next few cycles. The combination of increased filling and contractile force augmentation provides an immediate boost to stroke volume and, under certain circumstances, can lead to increased cardiac output. For this reason, ESS therapy delivery has been proposed as a therapy for patients with congestive heart failure (CHF), left ventricular dysfunction (LVD), cardiac insufficiency, post-resuscitation pulse-less electrical activity (PEA) or electro-mechanical dissociation (EMD), and the like.

On the other hand, delivery of ESS pacing pulses—particularly of relatively high magnitude—if delivered too close to or during the refractory period (e.g., the vulnerable period), can provoke an arrhythmia episode. As a result, delivery of ESS therapy, particularly to patients with CHF, LVD, PEA, EMD and/or cardiac insufficiency who may be more susceptible to an episode arrhythmia than the general population, must be carefully controlled with caution and using state-of-the-art pacing platforms.

SUMMARY

In general, the invention is directed to circuits for the delivery of pacing pulses via multiple pacing output channels. An external or an implantable medical device according to the invention, such as a cardiac pacemaker or implantable pulse generator (IPG), includes two or more pacing output channels coupled to a single unipolar electrode or bipolar electrode pair. Each pacing output channel can be independently controlled to, for example, deliver pacing pulses at different times and with different amplitudes.

Each pacing output channel includes a hold capacitor to store energy. A control circuit independently controls switches for each pacing output channel to control the charging and discharging of each capacitor, and the voltage stored on each capacitor. The control circuit selectively couples the hold capacitors to the respective electrodes for delivery of pacing pulses, enabling the delivery of pacing pulses from multiple pacing output channels at different times and with different amplitudes.

In some embodiments, the implantable medical device is used to deliver ESS therapy. In such embodiments, a first pacing output channel can be controlled to deliver pacing pulses with an amplitude sufficient to depolarize a chamber of the heart. A second pacing output channel is controlled to deliver extra-systolic pulses, which can have a lower amplitude than the pacing pulses. The extra-systolic pulses are delivered within an extra-systolic interval (ESI) after sensed or paced depolarizations of the chamber. The lower the amplitude of an extra-systolic pulse relative to a pacing threshold for the chamber (to ensure capture), the less likely it is to lead to an arrhythmia.

In some embodiments, the implantable medical device includes electrodes in the right and left ventricle and delivers cardiac resynchronization therapy (CRT) in addition to ESS therapy. In such embodiments, the control unit may control the coupling of two or more pacing output channels to the right and left ventricular electrodes to provide periods where either ESS therapy or CRT are delivered, e.g., switching between ESS therapy and CRT modes, and periods where both ESS therapy and CRT are delivered, e.g. by delivering extra-systolic pulses to one or both of the right and left ventricle an extra-systolic interval after delivery of CRT pacing pulses to one or both of the right and left ventricle.

In one embodiment, the invention is directed to a medical device that includes an electrode and at least two pacing output channels. Each pacing output channel includes a capacitor that stores energy for delivery as a pacing pulse to a heart of a patient via the electrode. The medical device also includes a control circuit that controls delivery of pacing pulses by selectively coupling the capacitors to the electrode.

In another embodiment, the invention is directed to method in which a first capacitor that stores energy is coupled to an electrode at a first time for delivery of a first pacing pulse to a heart, and a second capacitor that stores energy is coupled to the electrode at a second time for delivery of a second pacing pulse to the heart.

In another embodiment, the invention is directed to a medical device having first and second means for storing energy for delivery as pacing pulses. The medical device also includes means for coupling the first energy storage means to an electrode at a first time for delivery of a first pacing pulse to the heart, and for coupling the second energy storage means to the electrode at a second time for delivery of a second pacing pulse to the heart.

In another embodiment, the invention is directed to a method in which pacing pulses are delivered to a heart of a patient via a first pacing output channel, and ESS pulses are delivered to the heart via a second pacing output channel independent from the first pacing output channel.

A wide variety of locations and types of electrodes may be employed in practicing the present invention. For example, each electrode may be adapted to couple to a discrete portion of myocardial tissue of the interior or exterior of a heart chamber, a portion of a coronary sinus, the cardiac veins, a transvenous location, an epicardial location, a pericardial location, a subcutaneous location, a percutaneous location, and the like. The electrodes used for pacing or sensing may be coupled to one or more elongated, deployable medical electrical leads, a subcutaneous electrode array (SEA), a patch-type epicardial lead, a surface portion of a canister of an implantable medical device, and the like. The electrodes may comprise traditional so-called tip electrodes, ring electrodes, button electrodes and/or coil electrodes or the like.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
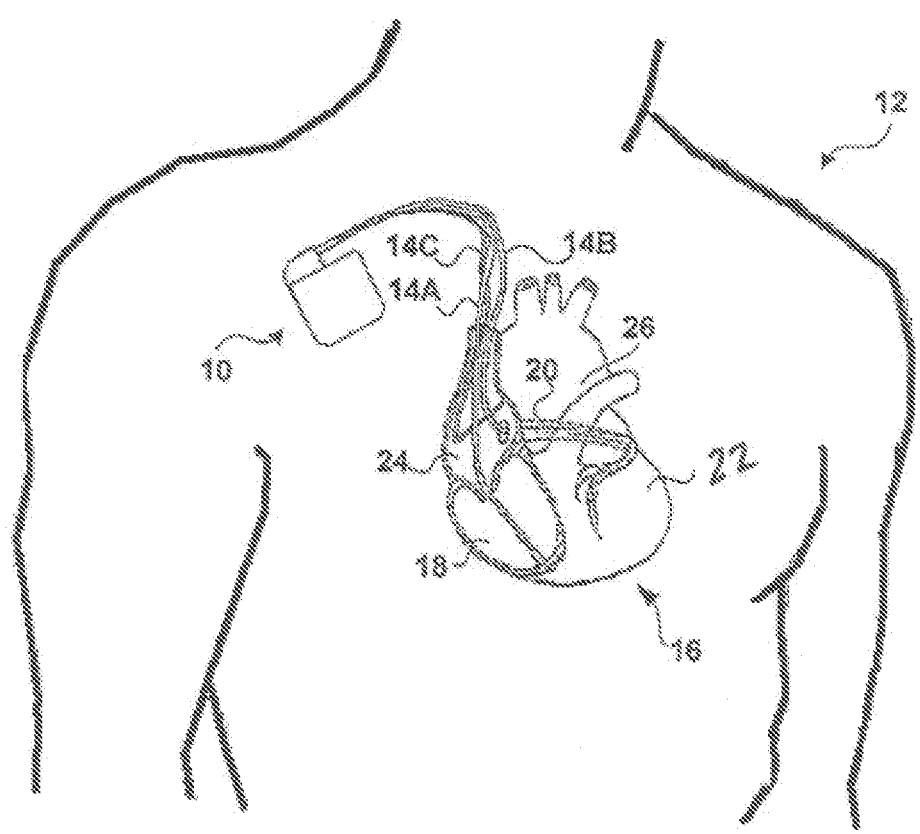
FIG. 1 is a conceptual diagram illustrating an exemplary implantable medical device implanted in a patient.

FIG. 1 is a conceptual diagram illustrating an exemplary implantable medical device (IMD) 10 implanted in a patient 12. IMD 10 can, as shown in FIG. 1, take the form of a multi-chamber cardiac pacemaker. As will be described, in accordance with the invention, IMD 10 includes two or more pacing output channels. Each pacing output channel can be independently controlled to, for example, deliver pacing pulses at different times and with different amplitudes. In the exemplary embodiment illustrated in FIG. 1, IMD 10 includes leads 14A, 14B, 14C (collectively "leads 14") that extend into the heart 16 of patient 12.

More particularly, right ventricular (RV) lead 14A extends through one or more veins (not shown), the superior vena cava (not shown), and right atrium 24, and into right ventricle 18. Left ventricular (LV) coronary sinus lead 14B extends through the veins, the vena cava, right atrium 24, and into the coronary sinus 20 to a point adjacent to the free wall of left ventricle 22 of heart 16. Right atrial (RA) lead 14C extends through the veins and vena cava, and into the right atrium 24 of heart 16.

Each of leads 14 includes electrodes (not shown), which IMD 10 uses to sense electrical signals attendant to the depolarization and repolarization of heart 16, and to provide pacing pulses to heart 16. In some embodiments, IMD 10 also provides cardioversion and defibrillation pulses via electrodes located on leads 14. The electrodes located on leads 14 can be unipolar or bipolar, as is well known in the art.

As will be described in greater detail below, at least one of the unipolar electrodes or bipolar electrode pairs uses to deliver pacing pulses to heart 16 is coupled to two or more pacing output channels. A pacing output channel includes circuitry for storage of energy, and delivery of the stored energy as a pacing pulse. Each pacing output channel is independently controllable. In other words, each pacing output channel coupled to a common unipolar electrode or bipolar electrode pair can be independently controlled to deliver pacing pulses via the electrode or electrode pair at selected times with selected pulse amplitudes.

In exemplary embodiments, IMD 10 delivers post extra-systolic pacing (ESS therapy delivery) therapy to patient 12 via one or more of leads 14. A first independently controlled pacing output channel of IMD 10 can deliver pacing pulses at a first amplitude sufficient to capture one of chambers 18, 22 and 24 via an electrode or electrode pair located on the respective one of leads 14. A second independently controlled pacing output channel of IMD 10 delivers extra-systolic pacing pulses to the chamber via the electrode or electrode pair during the relative refractory period after delivery of pacing pulses to the chamber by the first pacing output channel. The second independently controlled pacing output channel of IMD 10 also delivers extra-systolic pacing pulses to the chamber during the relative refractory period after sensed depolarizations of the chamber.

The extra-systolic pacing pulses delivered by the independently controlled second pacing output channel can have a second, lower amplitude than pacing pulses delivered by the first pacing output channel. In general, the lower the amplitude of pacing pulses delivered during the relative refractory period is, the less likely it is that those pacing pulses will trigger a potentially life-threatening tachyarrhythmia. Conventional pacemakers with a single pacing output channel per electrode or pair are generally unable to change the amount of energy stored after a sensed depolarization or recharge to a different amount of stored energy after delivery of a first pacing pulse quickly enough to allow delivery of extra-systolic pacing pulses at lower amplitudes. Consequently, delivery of ESS therapy via conventional pacemakers involves either unsafe extra-systolic pacing amplitudes, or the use of additional leads and electrodes, which undesirably increases the amount of foreign matter implanted within the patient. Thus, the inclusion of multiple independently controllable pacing output channels per electrode or electrode pair can enable IMD 10 to deliver ESS therapy more safely than conventional pacemakers.

The invention is not limited to any particular technique for delivering ESS therapy. IMD 10 can determine the interval between a paced or sensed depolarization and the delivery an extra-systolic pulse according to any known technique. ESS therapy delivery may be delivered only periodically, and IMD 10 may determine when and for how long to deliver ESS therapy according to any known techniques.

In some embodiments, IMD 10 delivers ESS therapy to treat CHF, LVD, PEA, EMD and/or cardiac insufficiency of patient 12. In such embodiments, IMD 10 can select the interval between a paced or sensed depolarization and the delivery of an extra-systolic pulse, and can determine when and for how long to deliver ESS therapy, based on one or more measured physiological parameters of patient 12 that indicate the status or progression of CHF or LVD. In an exemplary embodiment, IMD 10 delivers ESS therapy in accordance with the disclosure of commonly assigned and co-pending U.S. Pat. No. 5,213,098 and non-provisional U.S. patent application Ser. No. 10/322,792 filed 28 Aug. 2002 both of which are hereby incorporated herein.

In some embodiments, IMD 10 delivers ORT or other pacing regimens in addition to ESS therapy. Many patients that suffer from CHF or LVD develop a wide ORS complex resulting from a delayed activation of one of the ventricles 18 and 22, which can worsen heart failure symptoms. IMD 10 delivers ORT deliver pacing pulses to one or both of ventricles 18 and 22 within a predetermined atrioventricular (AV) delay after sensed or paced contractions of atria 24,26 in order to synchronize the contractions of ventricles 18,22. Where both of ventricles 18,22 are paced, the ventricles can be paced simultaneously or one of the ventricles can be paced a V-V interval after the other. IMD 10 uses multiple independently controllable pacing output channels to facilitate simultaneous delivery of ESS therapy delivery and CRT, and/or switching between delivery of ESS therapy delivery and CRT, as will be described in greater detail below.

The configuration of IMD 10 illustrated in FIG. 1 is merely exemplary. IMD 10 can include any number of leads 14, and each of leads 14 can extend to any location within or proximate to heart 16. For example, some embodiments of IMD 10 include a single lead 14A or 14C that extends into right ventricle 18 or right atrium 24, respectively, or two leads 14A, 14C that extend into the right ventricle 18 and right atrium 24, respectively. Other embodiments of IMD 10 include leads 14A–C located as illustrated in FIG. 1, and an additional lead 14 located within or proximate to left atrium 26. The number of leads 14 and their location depend on the therapy or therapies delivered by IMD 10, and the invention is not limited to any particular therapy or lead configuration.

Some embodiments include epicardial leads instead of or in addition to the transvenous leads 14 illustrated in FIG. 1. Further, IMD 10 need not be implanted within patient 12. Where IMD 10 is not implanted in patient 12, IMD 10 can deliver pacing pulses to heart 12 via percutaneous leads that extend through the skin of patient 12 to a variety of positions within or outside of heart 16, subcutaneous electrodes or transcutaneous electrodes placed on the skin of patient 12.

Figure 2:
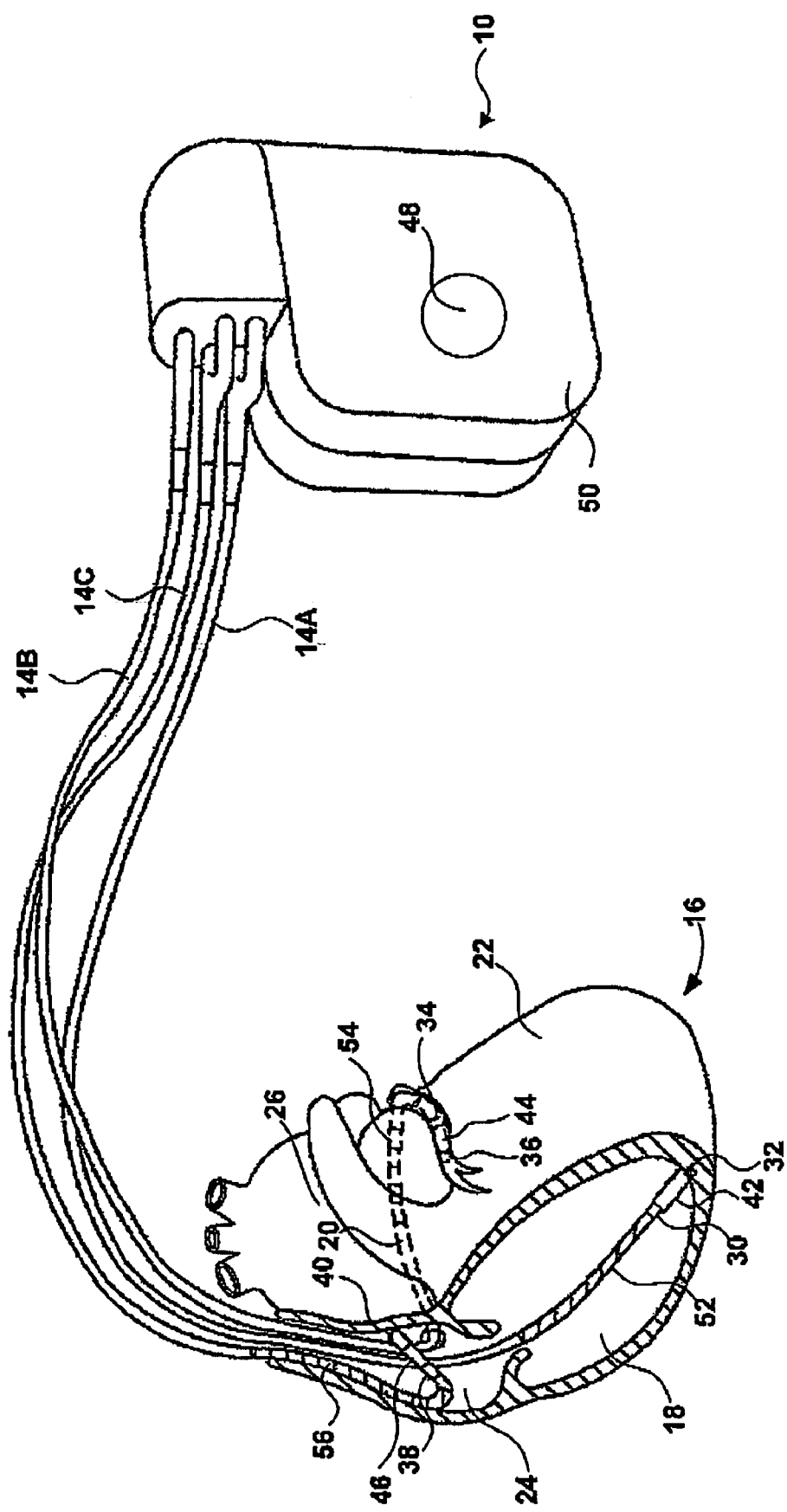
FIG. 2 is conceptual diagram further illustrating the implantable medical device of FIG. 1 and the heart of the patient.

FIG. 2 is conceptual diagram further illustrating IMD 10 and heart 16 of patient 12. Each of leads 14 includes an elongated insulative lead body carrying a number of concentric coiled conductors separated from one another by tubular insulative sheaths. Located adjacent distal end of leads 14A, 14B and 14C are bipolar electrodes 30 and 32, 34 and 36, and 38 and 40 respectively. Electrodes 30, 34 and 38 can take the form of ring electrodes, and electrodes 32, 36 and 40 can take the form of extendable helix tip electrodes mounted retractably within insulative electrode heads 42, 44 and 46, respectively. Each of the electrodes 30–40 is coupled to one of the coiled conductors within the lead body of its associated lead 14.

Sense/pace electrodes 30,32,34,36,38,40 sense electrical signals attendant to the depolarization and repolarization of heart 16. The electrical signals are conducted to IMD 10 via leads 14. Sense/pace electrodes 30,32,34,36,38,40 further may deliver pacing to cause depolarization of cardiac tissue. IMD 10 may also include one or more indifferent housing electrodes, such as housing electrode 48, formed integrally with an outer surface of the hermetically sealed housing 50 of IMD 10. Any of electrodes 30,32,34,36,38,40 may be used for unipolar sensing or pacing in combination with housing electrode 48.

As discussed above, at least one of bipolar electrode pairs 30 and 32, 34 and 36, and 38 and 40 is coupled to two or more pacing output channels. Each of the electrode pairs that are coupled to two or more pacing output channels is used to deliver ESS therapy, e.g., extra-systolic pulses following paced or sensed depolarizations, as discussed above. Where one or more of electrodes 32,36,40 is used to deliver pacing pulses in unipolar configuration with electrode 48 of housing 50, that electrode 32,36,40 and housing electrode 48 can be coupled to two or more pacing output channels, and can be used to deliver ESS therapy.

Leads 14A, 14B, 14C may also, as shown in FIG. 2, include elongated coil electrodes 52,54,56, respectively. IMD 10 may deliver defibrillation or cardioversion shocks to heart 16 via defibrillation electrodes 52–56. Defibrillation electrodes 52–56 are fabricated from platinum, platinum alloy or other materials known to be usable in implantable defibrillation electrodes, and may be about 5 cm in length.

Figure 3:
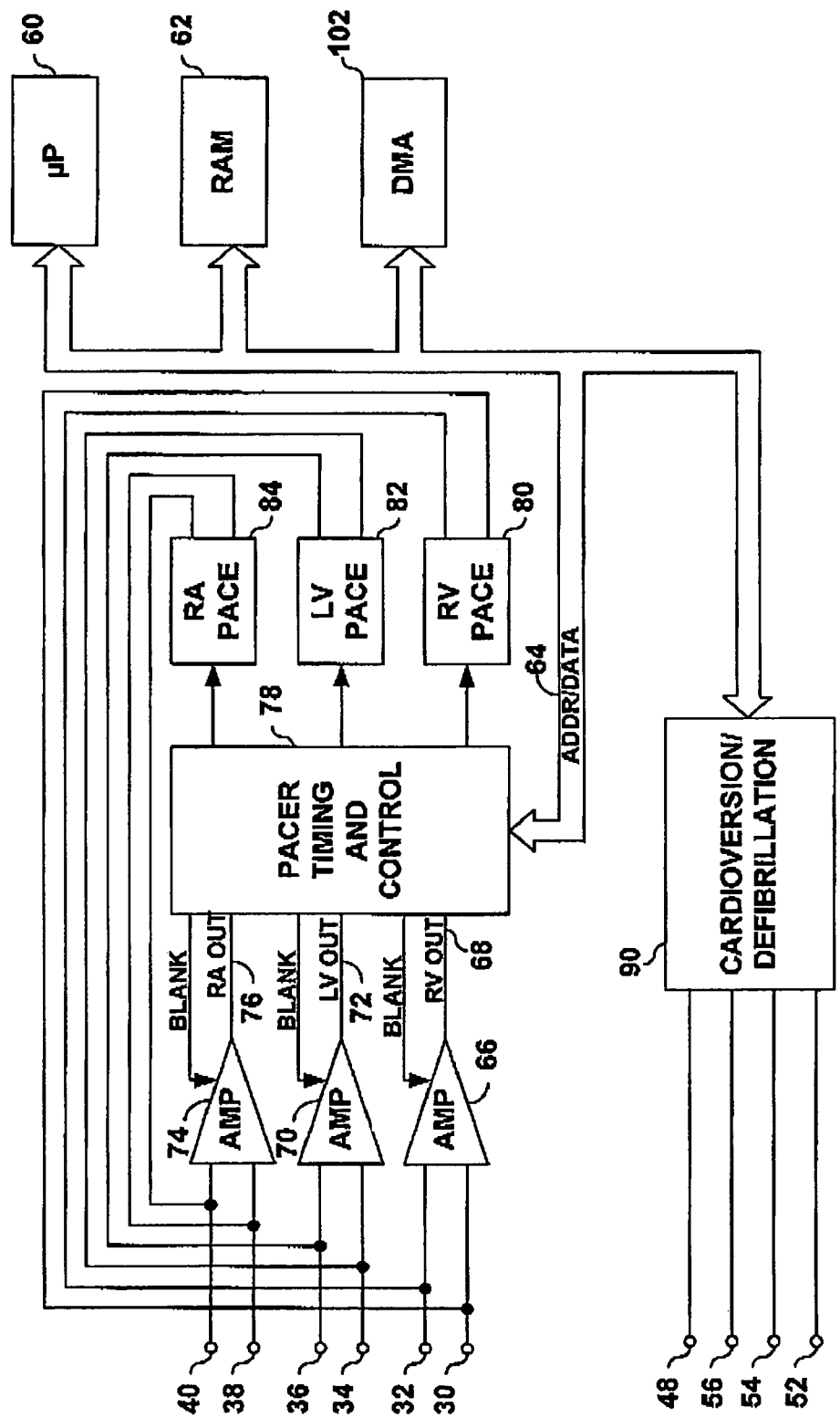
FIG. 3 is a functional block diagram of the implantable medical device of FIG. 1.

FIG. 3 is a functional block diagram of IMD 10. As shown in FIG. 3, IMD 10 can take the form of a multi-chamber pacemaker-cardioverter-defibrillator (PCD) having a microprocessor-based architecture. However, this diagram should be taken as exemplary of the type of device in which various embodiments of the present invention may be embodied, and not as limiting. For example, it is believed that the invention may be practiced in a wide variety of device implementations, including devices that provide ESS therapy, or ESS therapy and CRT, but not necessarily cardioverter and/or defibrillator functionality.

IMD 10 includes a microprocessor 60. Microprocessor 60 executes program instructions stored in memory, such as a ROM (not shown), EEPROM (not shown), and/or RAM 62, which control microprocessor 60 to perform the functions ascribed to microprocessor 60 herein. Microprocessor 60 is coupled to, e.g., to communicate with and/or control, various other components of IMD 10 via an address/data bus 64.

IMD 10 senses electrical activity within heart 16. Electrodes 30 and 32 are coupled to amplifier 66, which can take the form of an automatic gain controlled amplifier providing an adjustable sensing threshold as a function of the measured R-wave amplitude. A signal is generated on RV out line 68 whenever the signal sensed between electrodes 30 and 32 exceeds the present sensing threshold. Thus, electrodes 30 and 32 and amplifier 66 are used to detect intrinsic right ventricular depolarizations.

Electrodes 34 and 36 are coupled to amplifier 70, which also can take the form of an automatic gain controlled amplifier providing an adjustable sensing threshold as a function of measured R-wave amplitude. A signal is generated on LV out line 72 whenever the signal sensed between electrodes 34 and 36 exceeds the present sensing threshold. Thus, electrodes 34 and 36 and amplifier 70 are used to detect intrinsic left ventricular depolarizations.

Electrodes 38 and 40 are coupled to amplifier 74, which can take the form of an automatic gain controlled amplifier providing an adjustable sensing threshold as a function of the measured P-wave amplitude. A signal is generated on RA out line 76 whenever the signal between electrodes 38 and 40 exceeds the present sensing threshold. Thus, electrodes 38 and 40 and amplifier 74 are used to detect intrinsic atrial depolarizations.

IMD 10 paces heart 16. Output circuits 80–84 deliver pacing pulses to heart 16 via electrodes 30–40 under the control of pacer timing/control circuitry 78. Specifically, output circuit 80 is coupled to electrodes 30 and 32 to deliver pacing pulses to right ventricle 18 (FIGS. 1 and 2), output circuit 82 is coupled to electrodes 34,36 to deliver pacing pulses to left ventricle 22 (FIGS. 1 and 2), and output circuit 84 is coupled to electrodes 38,40 to deliver pacing pulses to right atrium 24 (FIGS. 1 and 2).

Output circuits 80–84 include capacitors and switches for the storage and delivery of energy as a pacing pulse. In conventional output circuits, the capacitors and switches form a single pacing output channel. At least one of output circuits 80–84, however, includes capacitors and switches that form at least one additional pacing output channel, as will be described in greater detail below.

Pacer timing/control circuitry 78 controls delivery of a pacing pulse by each of output circuits 80–84 by controlling the configuration of the switches therein. Specifically, pacer timing/control circuitry 78 configures the switches of an output circuit to cause a capacitor to charge until a selected energy level for a pacing pulse is met, determines when the pacing pulse is to be delivered, and, when the pacing pulse is to be delivered, configures the switches to allow the capacitor to discharge the stored energy across an electrode pair as a pacing pulse. An output circuit that includes an additional pacing output channel includes additional switches, and pacer timing/control circuitry 78 independently controls the additional switches to independently control the charging, amount of energy stored, and discharging of the additional capacitor.

Pacer timing/control circuitry 78 preferably includes programmable digital counters which control the basic time intervals associated with modes of pacing. Circuitry 78 also preferably controls escape intervals associated with pacing. In exemplary embodiments, circuitry 78 controls the interval between a paced or sensed depolarization and delivery of an extra-systolic pulse to heart 16 for delivery of ESS therapy. Circuitry 78 also controls atrial and/or ventricular escape intervals associated with a selected mode of pacing. In some embodiments, circuitry 78 controls an atrioventricular escape interval, and can also control a V-V interval for delivery of CRT.

Pacer timing/control circuitry 78 resets interval counters upon detection of R-waves or P-waves, or generation of pacing pulses, and thereby controls the basic timing of cardiac pacing functions. Intervals defined by pacing circuitry 78 may also include refractory periods during which sensed R-waves and P-waves are ineffective to restart timing of escape intervals, and the pulse widths of the pacing pulses. The durations of these intervals are determined by microprocessor 60 in response to data stored in RAM 62, and are communicated to circuitry 78 via address/data bus 64. The amplitude of the cardiac pacing pulses, e.g., the energy stored in capacitors of output circuits 80–84, is also determined by circuitry 78 under control of microprocessor 60.

Microprocessor 60 operates as an interrupt driven device, and is responsive to interrupts from pacer timing/control circuitry 78 corresponding to the occurrence of sensed P-waves and R-waves and corresponding to the generation of cardiac pacing pulses. Those interrupts are provided via data/address bus 66. Any necessary mathematical calculations to be performed by microprocessor 60 and any updating of the values or intervals controlled by pacer timing/control circuitry 78 take place following such interrupts.

As mentioned above, in some embodiments IMD 10 modifies or initiates ESS therapy based on one or measured physiological parameters of patient 12 that indicate the status or progression of CHF or LVD. In such embodiments, IMD 10 can include additional components and systems (not shown) to detect such physiological parameters. As examples, IMD 10 can include known sensors and circuitry to detect patient activity, respiration, thoracic impedance, blood pressure, or intracardiac pressure. IMD 10 can also use known techniques to analyze signals sensed in heart 16 to identify electrogram features that indicate cardiac function, such QRS complex widths and Q-T interval lengths. In an exemplary embodiment, IMD 10 includes sensors and circuits and controls ESS therapy as disclosed in the incorporated non-provisional U.S. patent application Ser. No. 10/232,792.

In some embodiments, IMD 10 detects ventricular and/or atrial tachycardias or fibrillations of heart 16 using tachycardia and fibrillation detection techniques and algorithms known in the art. For example, the presence of a ventricular or atrial tachycardia or fibrillation can be confirmed by detecting a sustained series of short R-R or P-P intervals of an average rate indicative of tachycardia, or an unbroken series of short R-R or P-P intervals. IMD 10 is also capable of delivering one or more anti-tachycardia pacing (ATP) therapies to heart 16, and cardioversion and/or defibrillation pulses to heart 16 via one or more of electrodes 48,52,54,56.

Electrodes 48,52,54,56, are coupled to a cardioversion/defibrillation circuit 90, which delivers cardioversion and defibrillation pulses under the control of microprocessor 60. Circuit 90 may include energy storage circuits such as capacitors, switches for coupling the storage circuits to electrodes 48,52,54,56, and logic for controlling the coupling of the storage circuits to the electrodes to create pulses with desired polarities and shapes. Microprocessor 60 may employ an escape interval counter to control timing of such cardioversion and defibrillation pulses, as well as associated refractory periods. IMD 10 may include cardioverter/defibrillator functionality where patient 12 has a history of tachyarrhythmia, or to address possibility of tachyarrhythmia associated with ESS therapy.

FIGS. 4–9 are circuit diagrams illustrating example output circuits that include two pacing output channels coupled to a single electrode pair. The illustrated output circuits can be used by IMD 10 to deliver pacing pulses to heart 16, and can correspond to any one or more of output circuits 80–84 described with reference to FIG. 3. Each of FIGS. 4–9 illustrates an example technique for providing two, independent pacing output channels and coupling the two pacing output channels to a single electrode or electrode pair. The invention is not, however, limited to the illustrated examples.

Figure 4:
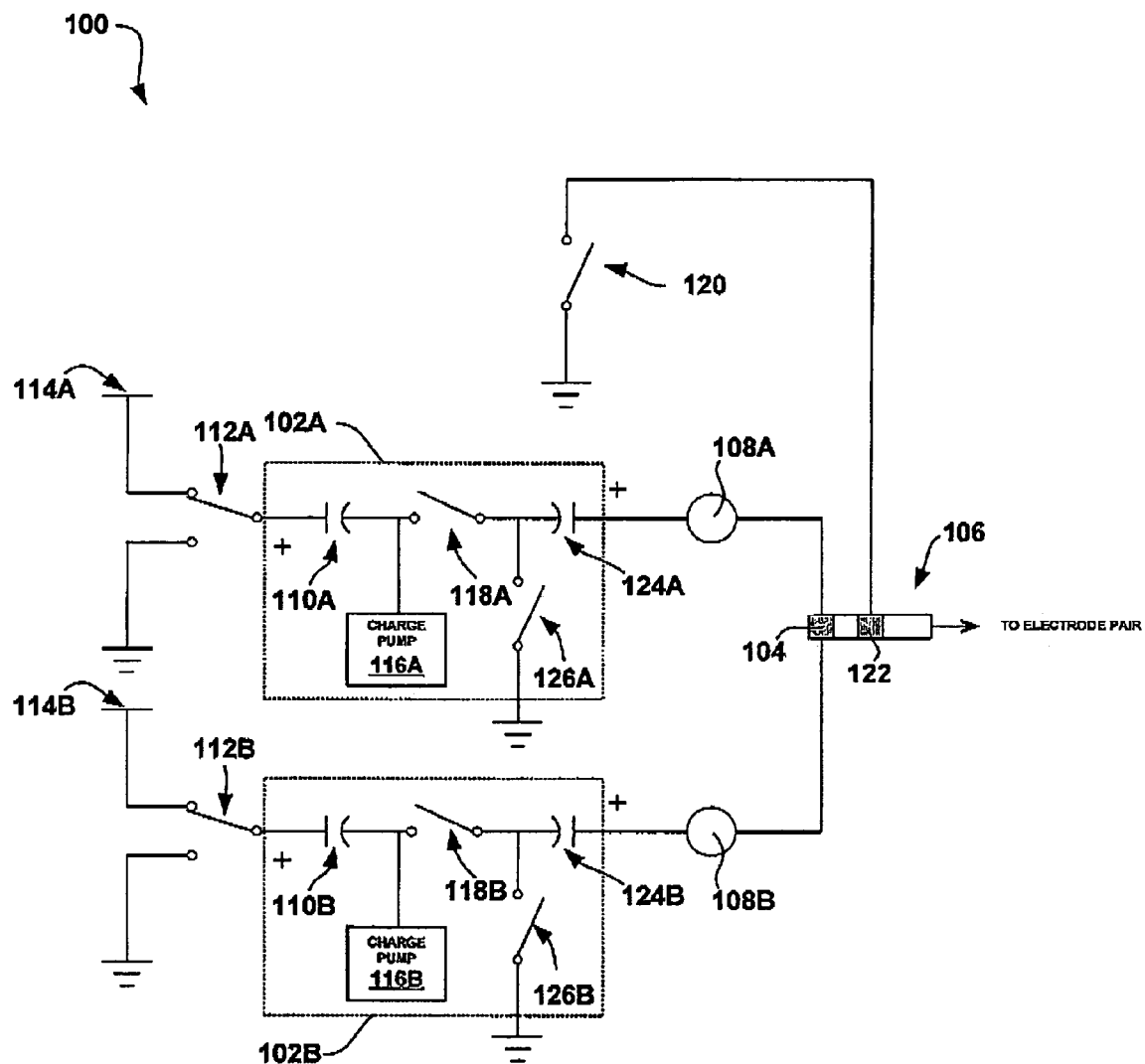
FIGS. 4–9 are circuit diagrams illustrating example output circuits that include two pacing output channels coupled to a single electrode pair and can be used by the implantable medical device of FIG. 1 to deliver pacing pulses to the heart.

FIG. 4 illustrates an output circuit 100 that includes two pacing output channels 102A and 102B (collectively "pacing output channels 102"). Both of pacing output channels 102A and 102B are coupled to an electrical contact 104 that is coupled to an electrode used to deliver pacing pulse to a heart. Electrical contact 104 is located at a header end 106 of one of leads 14, and is coupled to an electrode, such as one of tip electrodes 32,36,40, via a coiled conductor of the lead. Output channels 102A and 102B are coupled to respective weld blocks 106A and 106B, which are in turn coupled to electrical contact 104.

Pacing output channel 102A includes a hold capacitor 110A, and pacing output channel 102B includes a hold capacitor 110B. Each of the hold capacitors 110A and 110B (collectively "hold capacitors 110") store energy that can be delivered via the connected electrode as a pacing pulse. Pacer timing/control circuitry 78 (FIG. 3) controls the charging and discharging of hold capacitors 110 associated with the delivery of pacing pulses. More particularly, circuitry 78 controls the configuration of switches to control the charging and discharging of hold capacitors 110.

Pacer timing/control circuitry 78 controls switches 112A and 112B to couple capacitors 110A and 110B to voltages 114A and 114B (collectively "voltages 114") in order to initially charge capacitors 110A and 110B to voltages 114A and 114B, respectively. Circuitry 78 controls charge pumps 116A and 116B (collectively "charge pumps 116") to charge or discharge each of capacitors 110A and 110B from the initial voltages 114 to respective selected voltages. In other words, circuitry 78 can independently control charge pumps 116A and 116B to charge capacitors 110A and 110B to different selected voltages. In this manner, circuitry 78 can control delivery of pacing pulses by pacing output circuits 102A and 102B at different pulse amplitudes, which, in some embodiments, facilitates the delivery of ESS therapy by IMD 10. Circuitry 78 can include voltmeters (not shown) across each of hold capacitors 110 as feedback for controlling charge pumps 116.

In order to discharge the energy stored in hold capacitors 110 across heart 16 as pacing pulses, pacer timing/control circuitry 78 closes pacing switches 118A and 118B (collectively "pacing switches 118") to couple capacitors 110A and 110B, respectively, to electrical contract 104. Circuit 78 independently controls the position of each of pacing switches 118. In general, only one of pacing switches 118 is closed at a time to couple its respective hold capacitor 110 to electrical contact 104. In this manner, circuitry 78 controls independent delivery of pacing pulses by each of pacing output circuits 102A and 102B.

Whenever circuitry 78 controls one of pacing switches 118 to close, circuitry 78 controls a ground-path switch 120 to close. Ground-path switch 120 couples a second electrical contact 122 on header end 106 of the lead 14, which is coupled to an electrode such as ring electrodes 30,34,38, to ground. When ground-path switch 120 is closed, a path to ground for discharge of one of hold capacitors 110 across the connected electrode pair is provided.

Pacing circuits 102A and 102B include tip capacitors 124A and 124B (collectively "tip capacitors 124"), respectively. Hold capacitors 110A and 110B discharge across tip capacitors 124A and 124B, respectively. Tip capacitors 124 provide alternating current (AC) coupling to heart 16. Specifically, after discharge of one of hold capacitors 110, pacer timing/control circuitry 78 controls a respective one of recharge switches 126A and 126B to discharge a voltage on the respective one of tip capacitors 124. Discharge of tip capacitors 124 removes residual polarization of heart 16 caused by discharge of hold capacitors 110, i.e., delivery of a pacing pulse.

Figure 5:
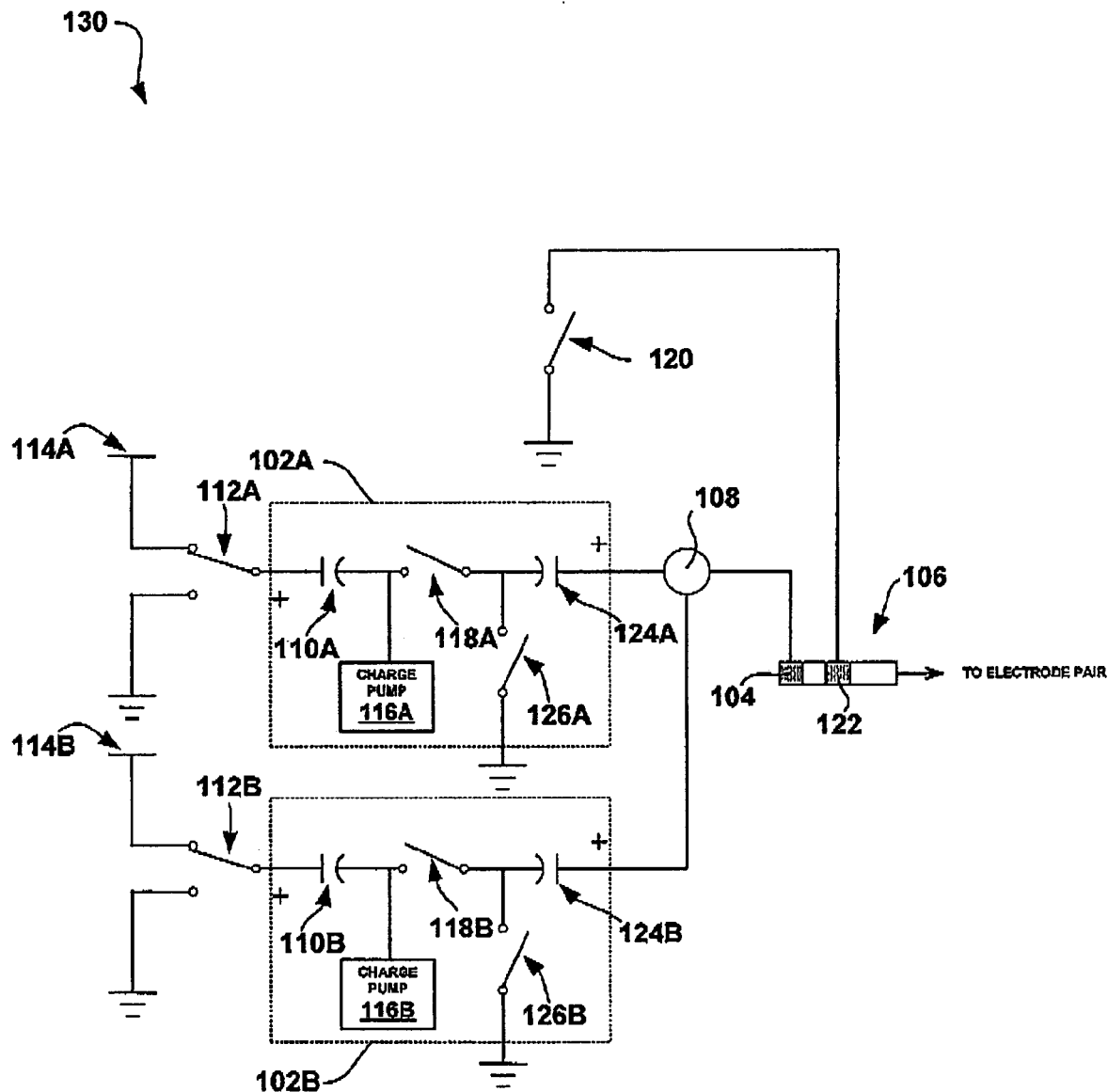
Figure 6:
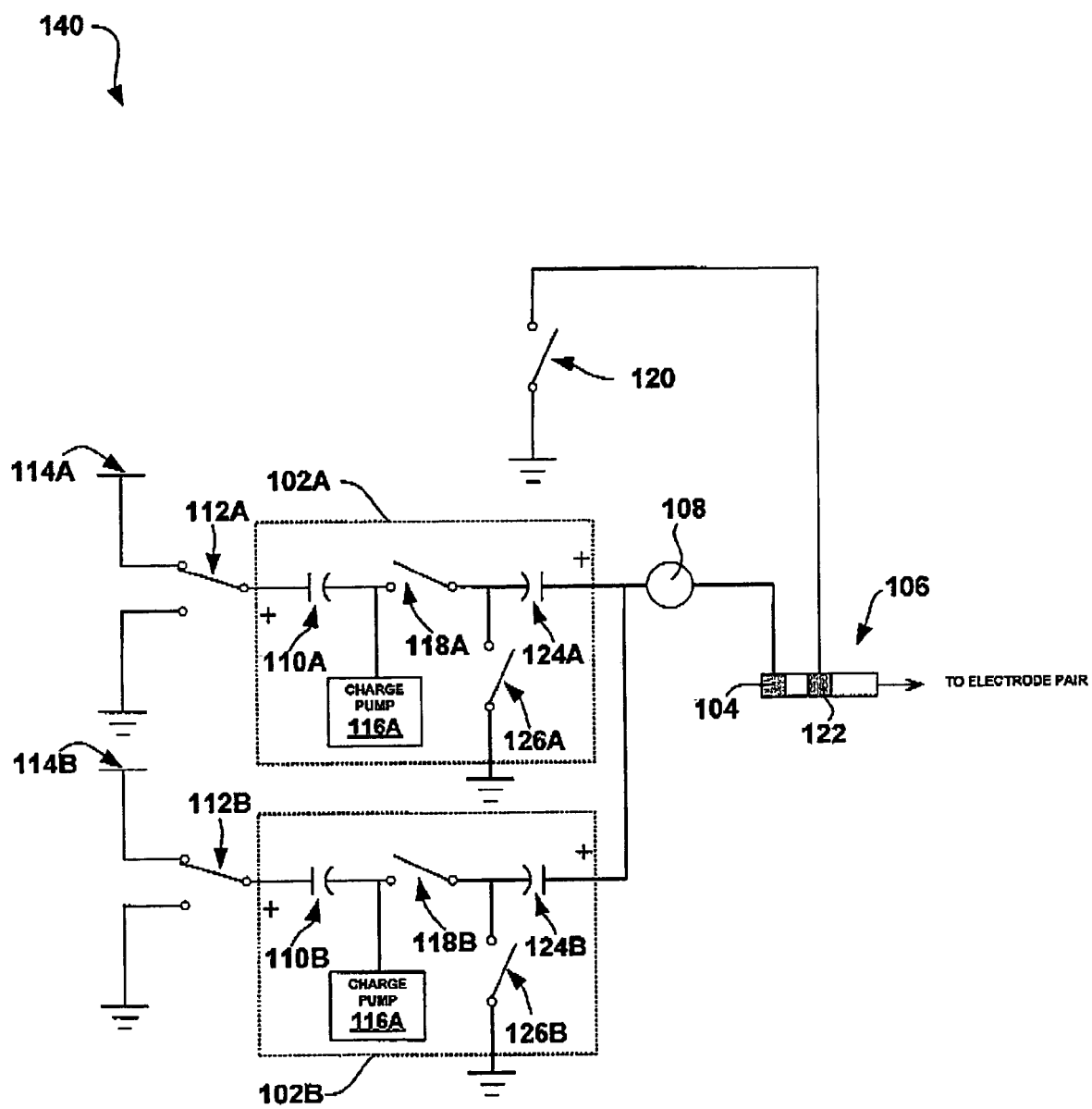

Example output circuits 130 and 140 of FIGS. 5 and 6 respectively illustrate that pacing output channels 102A and 102B can be electrically coupled to electrical contact 104 via a single weld block 108. Pacing output channels 102A and 102B can be commonly coupled at weld block 108, as illustrated by output circuit 130 of FIG. 5, or can be coupled to a shared conductive element that is in turn coupled to weld block 108, as illustrated by output circuit 140 of FIG. 6.

Figure 7:
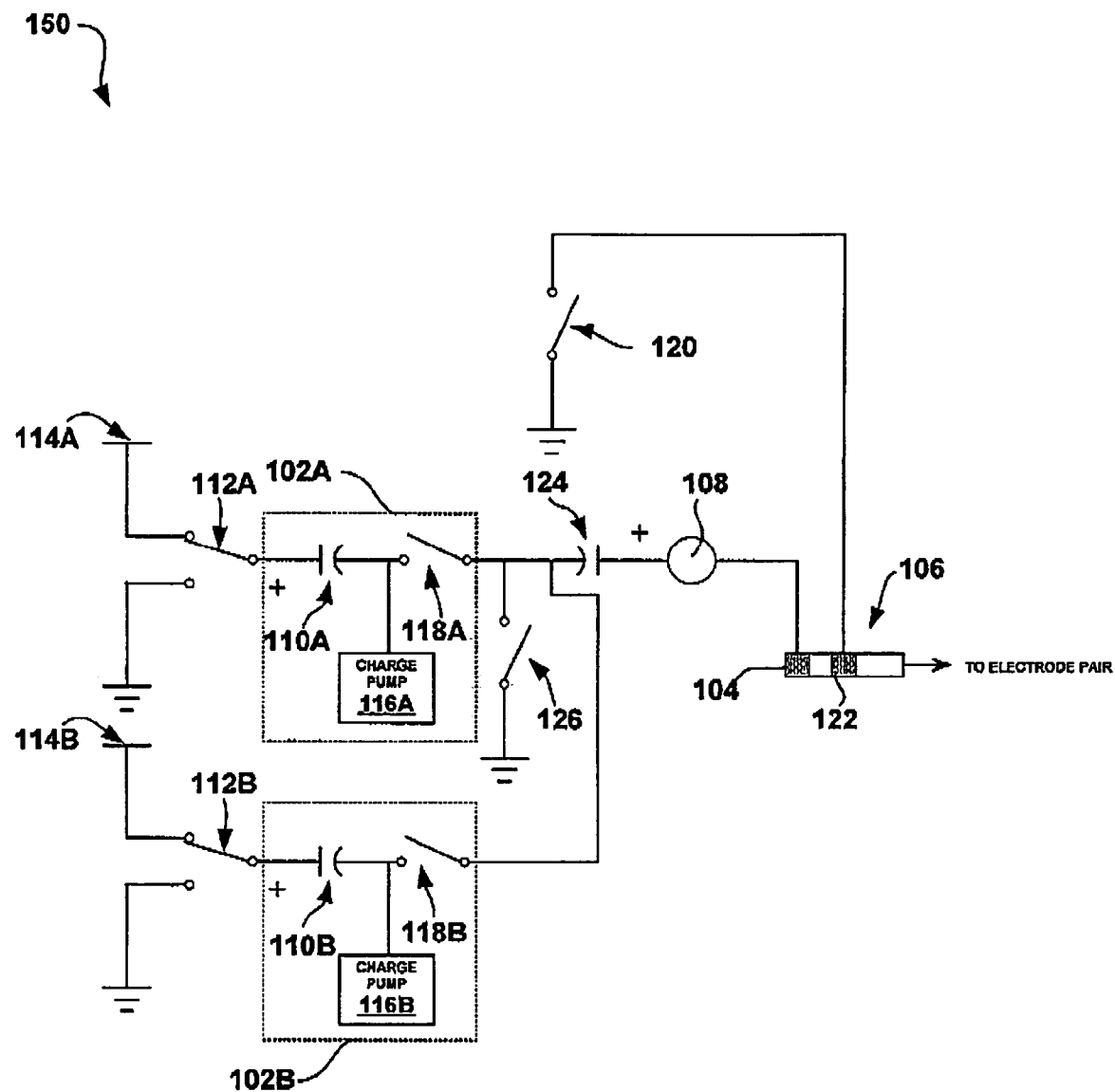

In an example output circuit 150 of FIG. 7, pacing output channels 102A and 102B do not include separate tip capacitors 124A and 124B. Instead, pacing output channels 102 are coupled to electrical contact 104 through a single tip capacitor 124, which provides AC coupling for delivery of pacing pulses by both of pacing output channels 102. Pacer timing/control circuitry 78 controls a single recharge switch 126 to discharge a voltage on tip capacitor 124 after delivery of a pacing pulse by either of pacing output channels 102A and 102B.

Figure 8:
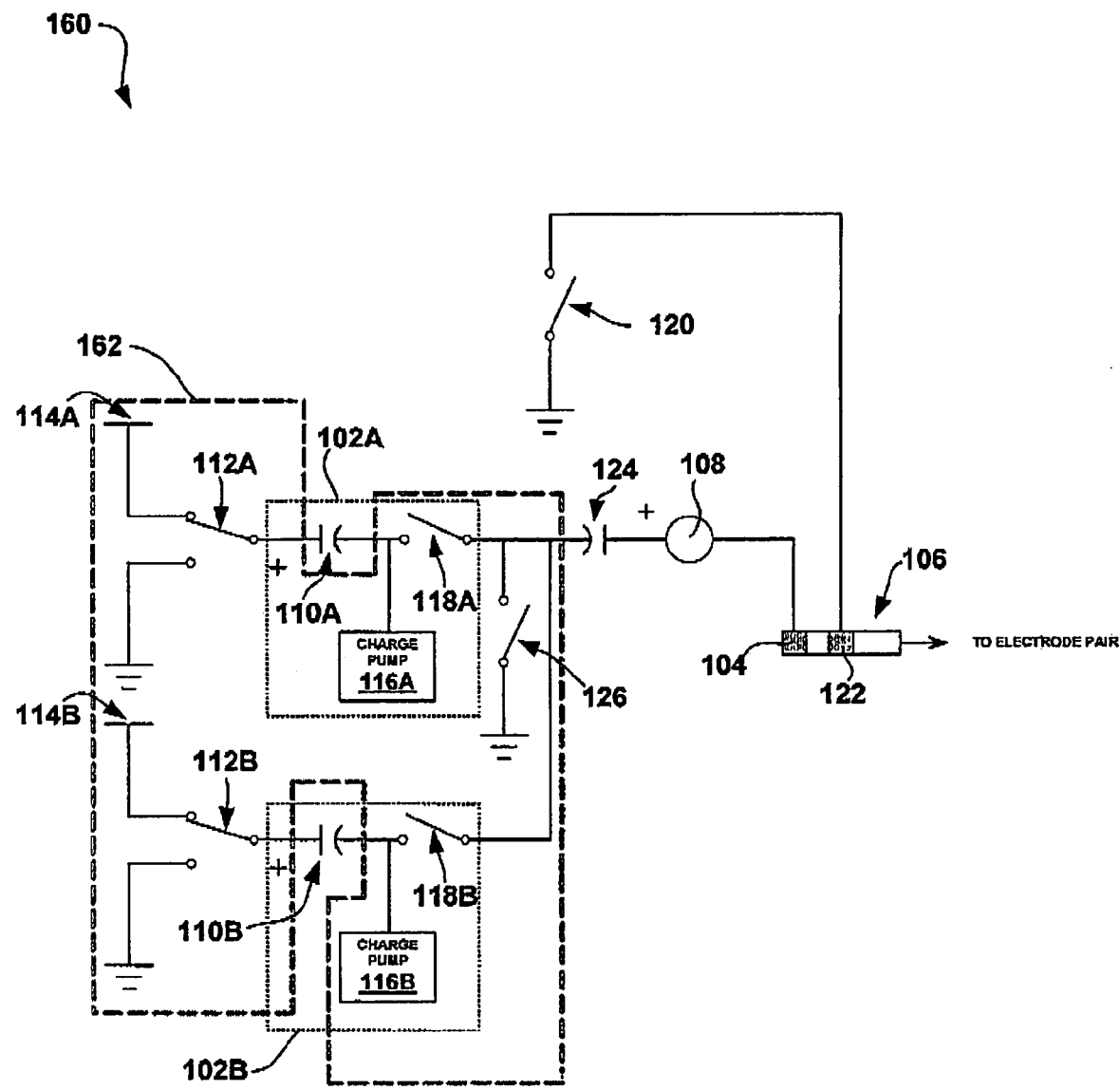
Figure 9:
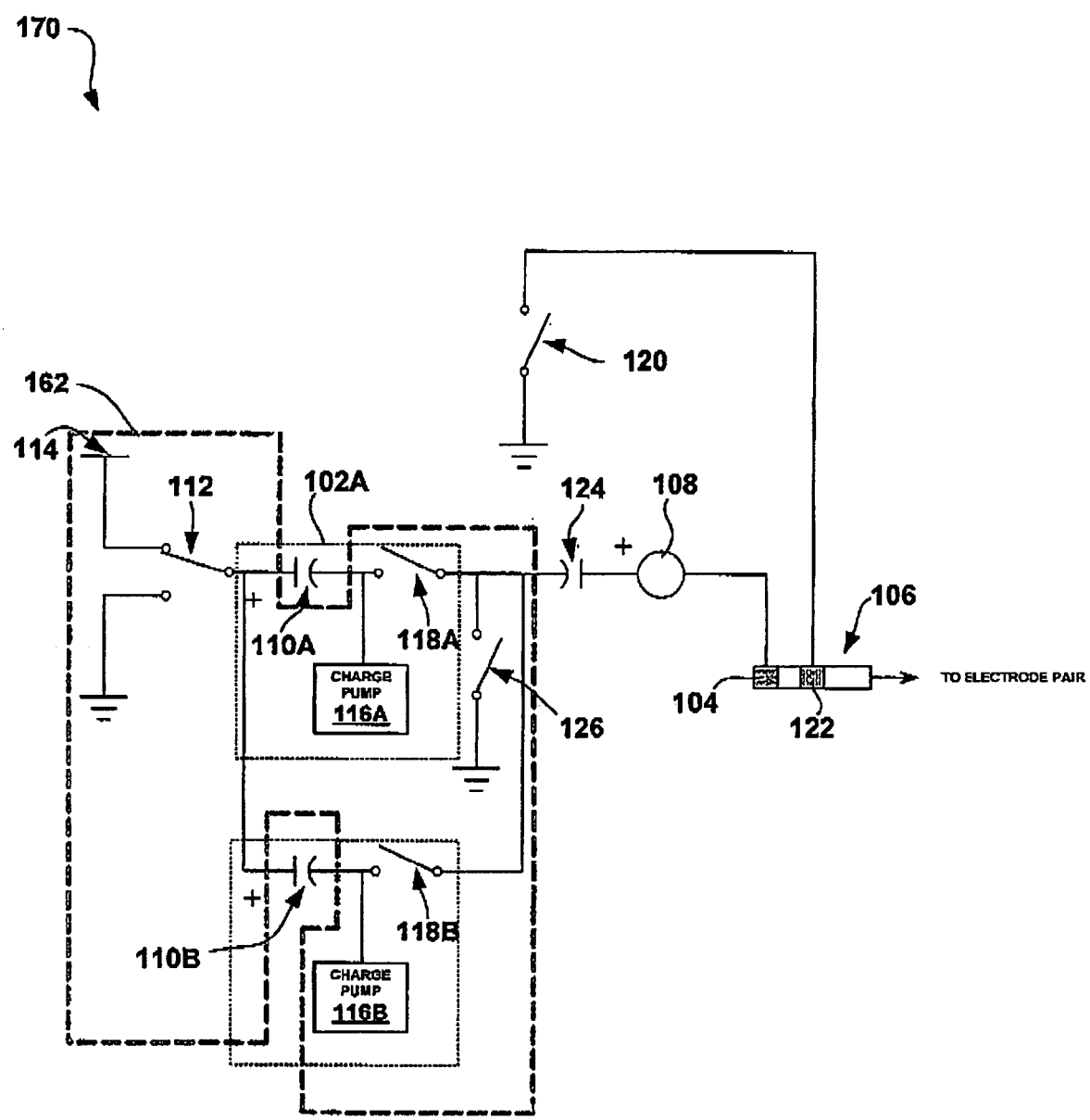

Other example output circuits 160 and 170 are illustrated in FIGS. 8 and 9, respectively. As illustrated in FIGS. 8 and 9, some components of output circuits 160 and 170, such as switches 112, 118 and 126, and charge pumps 116 are contained within an integrated circuit (IC) 162. In output circuits 160 and 170, pacing output channels 102A and 102B are coupled within IC 62, e.g., to a common conductive element within IC 62. Pacing output channels 102 can be, for example, coupled to a common output pin of IC 62.

Voltages 114 of output circuit 160, shown in FIG. 8, are provided to pins of IC 162. Pacer timing/control circuit 78 toggles switches 112 to selectively couple hold capacitors 110 to the pins. As shown in FIG. 9, hold capacitors 110 of output circuit 170 can be coupled to a single voltage 114, e.g., pin of IC 162, by their respective switches 112. IC 162 and the other components of output circuits 160 and 170 can be coupled to a hybrid circuit board. The illustrated components described herein as electrically coupled by conductive elements can be coupled by traces within IC 162, pins of IC 162, and traces within the hybrid circuit. Of the output circuit embodiments illustrated in FIGS. 4–9, output circuit 170 of FIG. 9 may be preferred because it utilizes the fewest components to provide two independently controllable pacing output channels 102 coupled to a single electrode pair.

Figure 10:
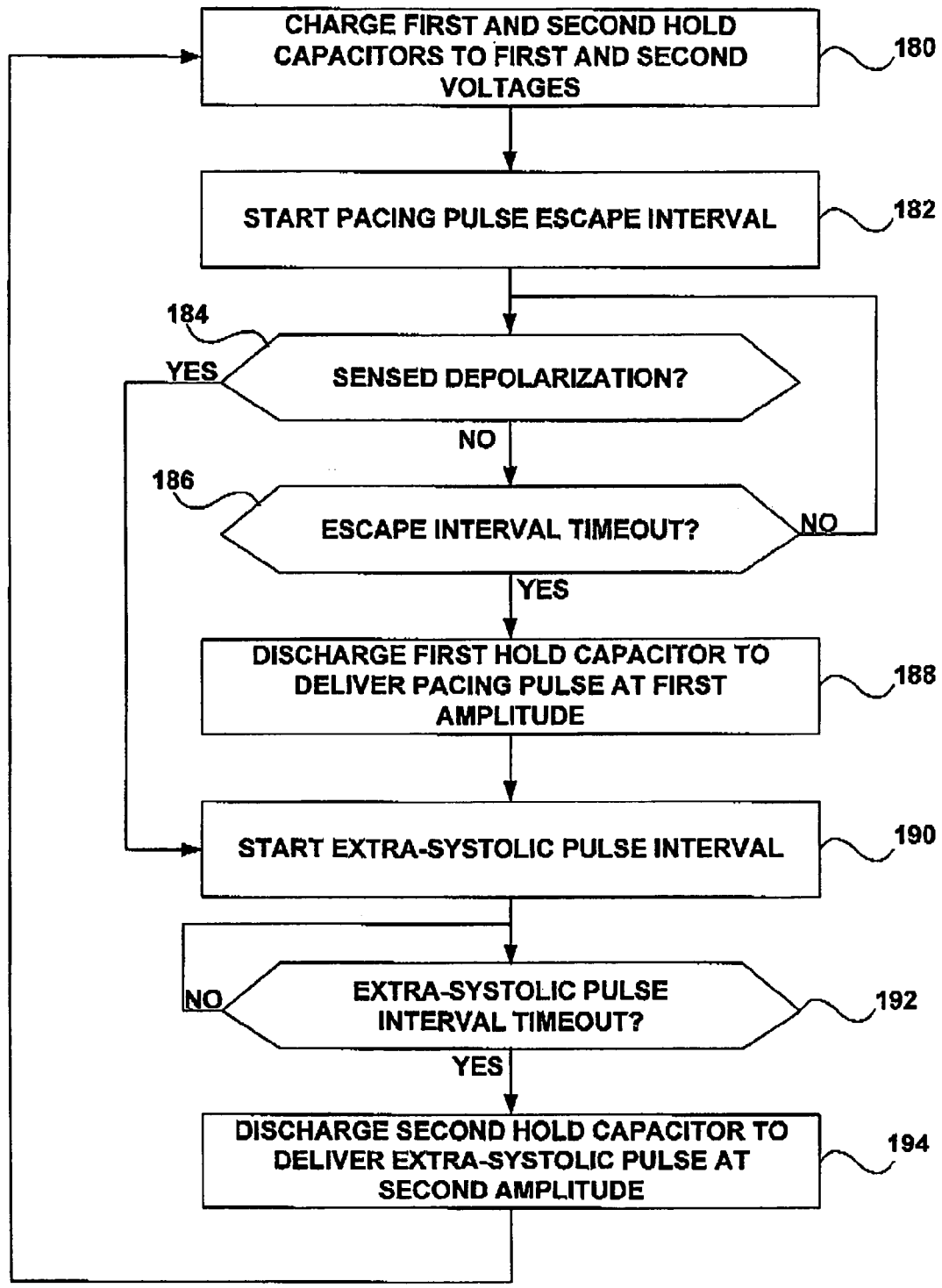
FIG. 10 is a flow chart illustrating an example method that can be employed by the implantable medical device of FIG. 1 to deliver post extra-systolic pacing (ESS therapy delivery) therapy using an output circuit that includes at least two pacing output channels coupled to a single electrode pair.

FIG. 10 is a flow chart illustrating an example method that can be employed by IMD 10 to deliver post extra-systolic pacing (ESS therapy delivery) therapy using an output circuit that includes at least two pacing output channels coupled to a single electrode pair, such as the exemplary output circuits illustrated FIGS. 4–9. Although the method is described with reference to output circuit 170 of FIG. 9, it is understood that an IMD including any the above-described output circuit configurations may utilize the method. Further, although the method is described with reference to delivery of pacing pulses to a single chamber of heart 16 via a single electrode pair, such as one of electrodes pairs, 30 and 32, 34 and 36, and 38 and 40, ESS therapy may be delivered to two or more chambers of heart 12 using two or more output circuits and two or more electrode pairs.

Pacer timing/control circuitry 78 (FIG. 3) controls the charging of hold capacitors 110 (180). Circuitry 78 controls toggles switch 112 to couple hold capacitors 110 to voltage source 114, which charges hold capacitors 110 to an initial voltage. Circuitry 78 then controls charge pumps 116 to charge or discharge respective hold capacitors 110 to respected selected voltages. Circuitry 78 can control charge pumps 116 to charge hold capacitors 110 to different voltages. For example, circuitry 78 can control charge pump 116A to charge hold capacitor 110A to a first voltage for delivery of a pacing pulse of sufficient amplitude to capture the chamber to which it is delivered, and can control charge pump 116B to charge hold capacitor 110B to a second voltage that is less then the first voltage for delivery of an extra-systolic pulse. The lower amplitude of the extra-systolic pulse may reduce the probability of the arrhythmia resulting from delivery of ESS therapy.

Circuitry 78 receives the selected voltages from processor 60 via data/address bus 64. In some embodiments, the voltages are voltages selected by a user and stored in a memory, such as RAM 62. In other embodiments, processor 60 selects the extra-systolic pulse voltage based on measured physiological parameters of patient 12 and information stored in memory.

Pacer timing/control circuitry 78 also starts an escape interval counter for a pacing pulse (182). Circuitry 78 waits for an indication of an intrinsic depolarization of the chamber of heart 16 from one of sensing amplifiers 72, 74 and 76 during the escape interval (184). If no indication is received before the escape interval times out (186), circuitry 78 toggles switch 118A to couple hold capacitor 110A to electrical contact 104 and closes ground-path switch 120 so that hold capacitor 110A is discharged across the electrode pair. In this manner, a pacing pulse with a first pulse amplitude is delivered to heart 16 via the electrode pair (188).

When a depolarization is sensed, or when the pacing pulse is delivered, pacer timing/control circuit 78 starts an extra-systolic pulse interval counter (190). Upon expiration of the extra-systolic pulse interval (192), circuitry 78 toggles switch 118B to couple hold capacitor 110B to electrical contact 104 and closes ground-path switch 120 so that hold capacitor 110B is discharged across the electrode pair. In this manner, an extra-systolic pulse with a second pulse amplitude is delivered to heart 16 via the electrode pair (194).

Figure 11:
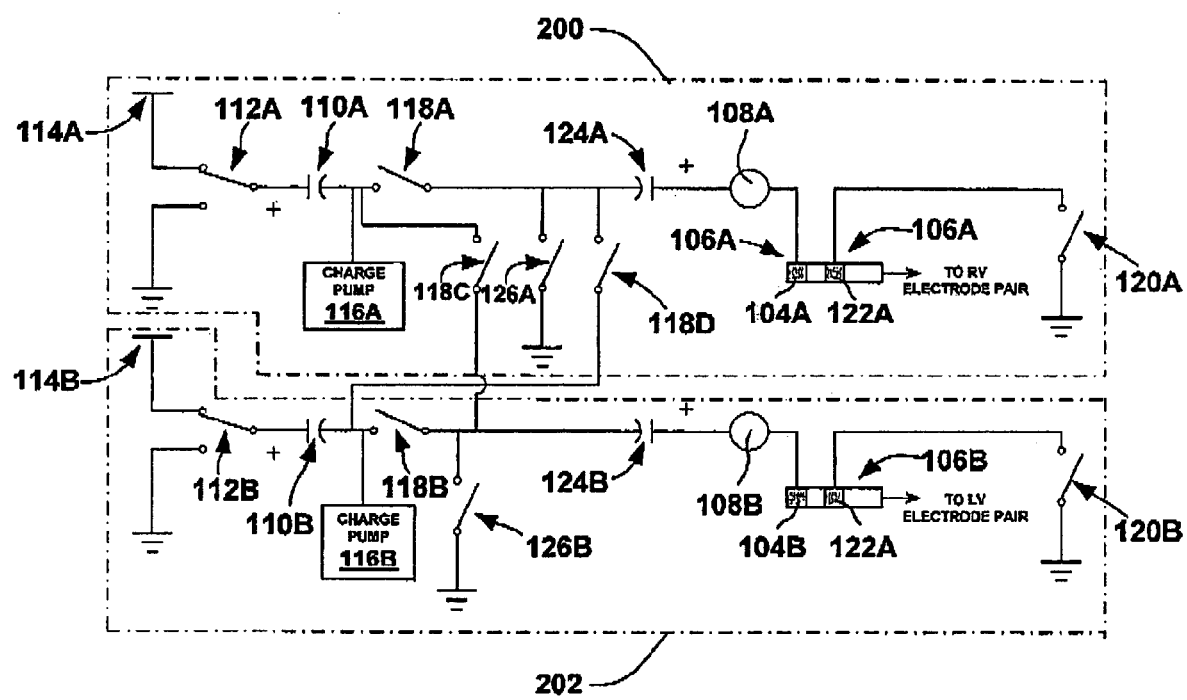
FIG. 11 is a circuit diagram illustrating example output circuits that are selectively coupled to provide an implantable medical device with two pacing output channels per electrode pair.

FIG. 11 is a circuit diagram illustrating example output circuits 200 and 202. Output circuits 200 and 202 are coupled to unipolar electrode or bipolar electrode pair located within or proximate to right ventricle 18 and left ventricle 22, respectively. Output circuits 200 and 202 may correspond to output circuits 80 and 82 of IMD 10 (FIG. 3), which are coupled to electrode pairs 30,32 and 34,36.

As shown in FIG. 11, each of output circuits 200 and 202 includes a single pacing output channel. The pacing output channels of output circuits 200 and 202 are configured substantially similarly to pacing output channels 102A and 102B illustrated in FIGS. 4–9. However, the pacing output channels of output circuits 200 and 202 are not solely coupled to a single electrode pair via a single electrical contact 104, as was the case with pacing output channels 102.

Instead, IMD 10 is capable of selectively coupling the pacing output channels of each of output circuits 200 and 202 to the other of output circuits 200 and 202 to provide two pacing output channels per electrode pair. Specifically, pacer timing/control circuit 78 can close pacing switch 118C of output circuit 200 to couple hold capacitor 110A to electrical contact 104B of output circuit 202 to discharge hold capacitor 110A across LV electrodes 34 and 36, and can close switch 118D of output circuit 202 to couple hold capacitor 110B to electrical contact 104A of output circuit 200 to discharge hold capacitor 110B across RV electrodes 30 and 32. The ability to selectively couple the pacing output channels of each of output circuits 200 and 202 to the other of output circuits 200 and 202 enables a variety of pacing therapy modes.

For example, IMD 10 can deliver ESS therapy to either right ventricle 18 or left ventricle 22. Pacer timing/control circuitry 78 controls charge pumps 116 to charge hold capacitors 110 to respective voltages. Independent of which of chambers 18 and 22 is receiving the pulses, either output circuit 200,202 can be controlled to deliver the pacing pulses or the extra-systolic pulses. If ESS therapy is delivered to left ventricle 22, circuit 78 holds pacing switch 118A open and selectively closes pacing switch 118C to couple hold circuit 110A to head end electrical contact 104B for delivery of either pacing or extra-systolic pulses. If ESS therapy is delivered to right ventricle 18, circuit 78 holds pacing switch 118B open and selectively closes pacing switch 118D to couple hold circuit 110B to head end electrical contact 104A for delivery of either pacing or extra-systolic pulses.

IMD 10 can deliver CRT using output circuits 200,202. Pacer timing/control circuitry 78 holds pacing switches 118C and 118D open, and selectively closes pacing switches 118A and 118B to couple hold capacitors 110A and 110B to their respective electrical contacts 104A and 104B. In this manner, output circuit 200 delivers pacing pulses to right ventricle 18, and output circuit 202 delvers pacing pulses to left ventricle 22. For CRT, pacing pulses can be delivered by one of output circuits 200 and 202 a V—V delay after delivery of a pacing pulse by the other of output circuits 200 and 202, e.g., a V—V delay may separate closure of switches 118A and 118B.

IMD 10 can switch between periods of delivering ESS therapy and periods of delivering CRT through control of switches 118A-D by pacer timing/control circuitry 78. In some embodiments, IMD 10 delivers CRT and ESS therapy at the same time. In such embodiments, each of output circuits 200,202 delivers a pacing pulse to its respective one of chambers 18 and 22 for CRT, and one of output circuits 200 and 202 additionally delivers an extra-systolic pulse to the other of chambers 18,22, e.g., one of hold capacitors 110 recharged and one of switches 118C and 118D closed, an interval after delivering a pacing pulse.

The one of output circuits 200 and 202 delivering the extra-systolic pulse may deliver both its pacing pulse and the extra-systolic pulses at the same amplitude, which may be a lower amplitude relative to the pacing pulse delivered by the other of output circuits 200 and 202 to reduce the probability of arrhythmia resulting the extra-systolic pacing. IMD 10 can switch between periods of CRT, periods of ESS therapy delivery, and periods of where both CRT and ESS therapy delivery are delivered. In some embodiments, IMD 10 can include only one of switches 118C and 118D, restricting delivery of ESS therapy to one of chambers 18 and 22.

Figure 12:
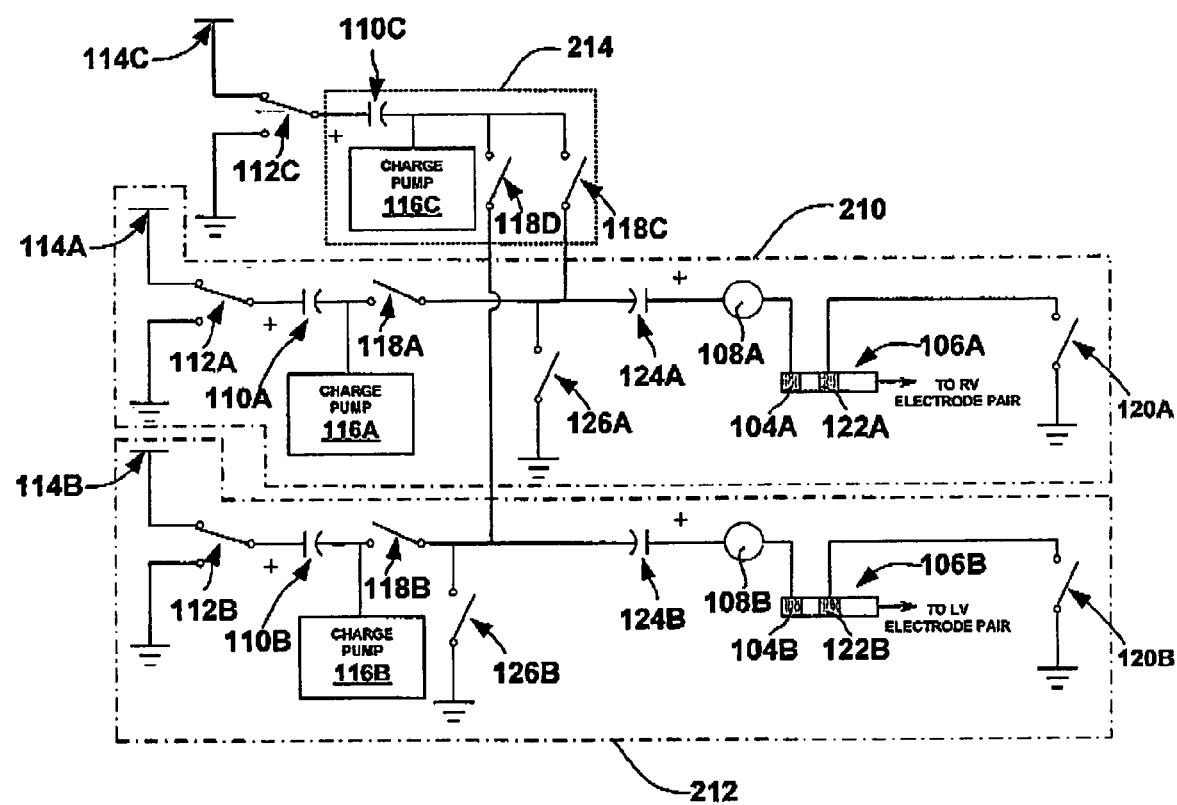
FIG. 12 is a circuit diagram illustrating example output circuits that are selectively coupled to a common additional pacing output channel to provide an implantable medical device with two pacing output channels per electrode pair.

FIG. 12 is a circuit diagram illustrating example output circuits 210 and 212, which are coupled to unipolar electrode or bipolar electrode pair located within or proximate to right ventricle 18 and left ventricle 22, respectively, and may correspond to output circuits 80 and 82 of IMD 10 coupled to electrode pairs 30, 32 and 34, 36. In the illustrated embodiments, hold capacitors 110 of output circuits 210 and 214 are not selectively coupled by switches to each other's electrical contacts 104 as discussed with reference to output circuits 200 and 202 of FIG. 11. Instead, IMD 10 includes an additional pacing output channel 214 with a hold capacitor 110C that can be selectively coupled to either or both of electrical contacts 104A and 104B of output circuits 210 and 212 by switches 118C and 118D, respectively.

In some embodiments, IMD 10 provides ESS therapy to patient 12 by controlling pacing output channel 214 to deliver an extra-systolic pacing pulse to one or both of ventricles 18 and 20 an extra-systolic interval after delivery of a pacing pulse to one of the ventricles by one of output circuits 210 and 212. Pacer timing/control circuitry 78 can control charging of one of hold capacitors 110A and 110B to a first voltage for a pacing pulse, and control charging of hold circuit 110C to a second voltage for an extra-systolic pulse. If an intrinsic ventricular depolarization is not sensed, circuitry 78 closes one of pacing switches 118A and 118B to discharge the charged one of hold capacitors 110A and 110B for delivery of a pacing pulse to one of ventricles 18 and 22. Following expiration of an extra-systolic interval initiated upon the detection of a sensed or paced depolarization, circuitry 78 closes one or both of pacing switches 118C and 118D to discharge hold capacitor 110C for delivery of an extra-systolic pulse to one or both of ventricles 18 and 22.

IMD 10 can also deliver CRT therapy via output circuits 210 and 212 in the manner described above with reference to output circuits 200 and 202 of FIG. 11, and can switch between periods of CRT and ESS therapy delivery. Further, IMD 10 can deliver CRT with ESS therapy by delivering extra-systolic pulses to one or both of ventricles 18 and 22, as described above, an extra-systolic interval after delivery of one of the pacing pulses delivered to the ventricles 18 and 22 for CRT therapy. As mentioned above, the pacing pulses delivered for CRT therapy can be delivered with a V—V interval therebetween.

Figure 13:
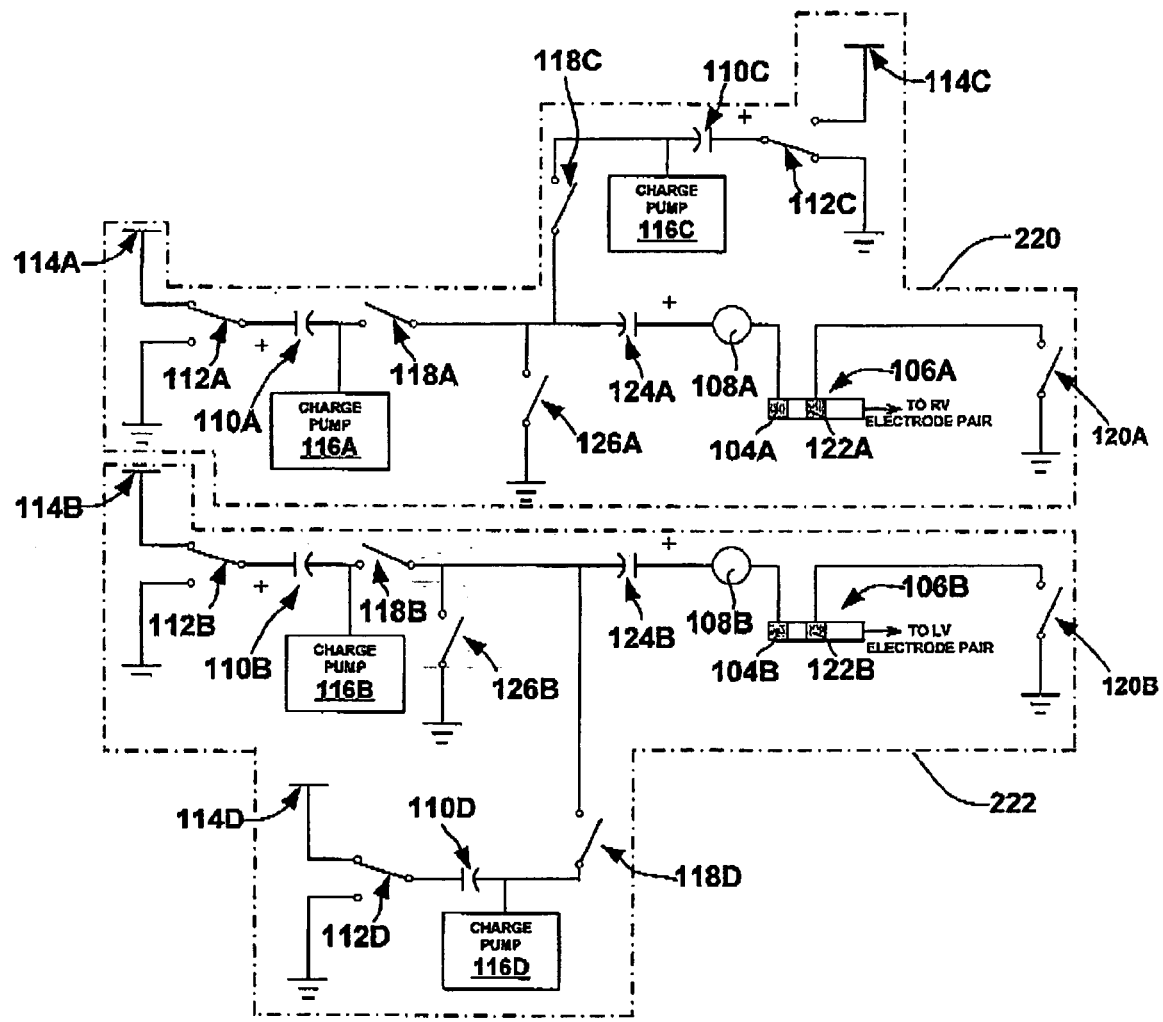
FIG. 13 is a circuit diagram illustrating example output circuits that include two pacing output channels per electrode pair.

FIG. 13 is a circuit diagram illustrating example output circuits 220 and 222, which are coupled to a unipolar electrode or bipolar electrode pair located within or proximate to right ventricle 18 and left ventricle 22, respectively, and may correspond to output circuits 80 and 82 of IMD 10 coupled to electrode pairs 30, 32 and 34, 36. As illustrated in FIG. 13, each of output circuits 220 and 222 includes two pacing output channel, e.g., two hold capacitors 110. In addition to switching between or providing a combination of ESS therapy and CRT as described above, output circuits 220 and 222, each with two pacing output channels, enable IMD 10 to deliver extra-systolic pulses to each of ventricles 18 and 22 at different times and with different amplitudes. For example, where IMD 10 delivers CRT combined with ESS therapy and the CRT includes delivery of pacing pulse to ventricles 18 and 22 at different times, IMD 10 can deliver extra-systolic paces to each of ventricles 18 and 22 an extra-systolic pacing interval after a sensed depolarization of, or delivery of the pacing pulse to, that ventricle.

Various embodiments of the invention have been described. For example, an IMD that includes two or more pacing output channels coupled to a single unipolar electrode or bipolar electrode pair has been described. Embodiments used to deliver ESS therapy to a patient, and embodiments used to deliver ESS therapy in combination with CRT to a patient have been described. However, the invention is not limited to the described embodiments, and one skilled in the art will recognized that various modifications can be made to the described embodiments without departing from the scope of the invention. For example, an IMD that includes two or more pacing output channels coupled to a single unipolar electrode or bipolar electrode pair can be used to deliver cardiac pacing therapies other that ESS therapy delivery or ESS therapy delivery in combination with CRT.

Certain therapies, such as antitachycardia pacing, require delivery of pacing pulses to the heart via a single electrode or electrode pair in rapid sequence. Conventional pacemakers having a single pacing output channel can have difficulty repeatedly recharging the single hold capacitor to an adequate voltage. Two or more pacing output channels coupled to the single electrode or electrode pair can be charged and discharged in a cascade to deliver the required pulse train, and to allow greater recharge time for each hold capacitor of the pacing output channels. These and other embodiments are within the scope of the following claims.

As is often practiced in the art, the methods according to the present invention may be implemented in any suitable processor-based architecture as executable instructions stored on a computer readable medium. Accordingly, the methods of the present invention expressly include all forms of computer readable media for storing such instructions.

The invention claimed is:

1. A method comprising:
 coupling a first capacitor that stores energy to an electrode at a first time for delivery of a first pacing pulse to a heart; and
 coupling a second capacitor that stores energy to the electrode at a second time for delivery of a second pacing pulse to the heart, wherein the electrode is a first electrode, the method further comprising coupling the second capacitor to a second electrode for delivery of a first cardiac resynchronization therapy pacing pulse, and
 wherein coupling the first capacitor to the first electrode comprises coupling the first capacitor to the first electrode for delivery of a second cardiac resynchronization therapy pacing pulse, and coupling the second capacitor to the first electrode comprises coupling the second capacitor to the first electrode for delivery of an extra-systolic pulse.

2. A method according to claim 1, further comprising detecting an intrinsic depolarization of the heart via the electrode, wherein coupling the second capacitor comprises coupling the second capacitor to the heart following expiration of an extra-systolic interval after the detection to deliver an extra-systolic pulse to the heart.

3. A method according to claim 1, wherein coupling the first capacitor comprises coupling the first capacitor to the heart upon expiration of an escape interval to deliver a pacing pulse to the heart, and coupling the second capacitor comprises coupling the second capacitor to the heart following expiration of an extra-systolic interval after delivery of the pacing pulse to deliver an extra-systolic pulse to the heart.

4. A method according to claim 3, wherein an amplitude of the extra-systolic pulse is less than an amplitude of the pacing pulse.

5. A method according to claim 1, wherein the electrode is one electrode of an electrode pair and wherein said one electrode is adapted to couple to the heart in one of the following locations: an endocardial location, an epicardial location, a transvenous location, a subcutaneous location, a pericardial location, a location within a cardiac vein, a location within a coronary sinus.

6. A method comprising:
 coupling a first capacitor that stores energy to an electrode at a first time for delivery of a first pacing pulse to a heart; and
 coupling a second capacitor that stores energy to the electrode at a second time for delivery of a second pacing pulse to the heart, wherein the electrode is a first electrode, the method further comprising coupling a third capacitor to a second electrode for delivery of a first cardiac resynchronization therapy pacing pulse, and wherein coupling the first capacitor to the first electrode comprises coupling the first capacitor to the first electrode for delivery of a second cardiac resynchronization therapy pacing pulse, and coupling the second capacitor to the first electrode comprises coupling the second capacitor to at least one of the first and second electrodes for delivery of an extra-systolic pulse.

7. A method comprising:

coupling a first capacitor that stores energy to an electrode at a first time for delivery of a first pacing pulse to a heart; and coupling a second capacitor that stores energy to the electrode at a second time for delivery of a second pacing pulse to the heart, wherein the electrode is a first electrode, the method further comprising coupling a third capacitor to a second electrode for delivery of a first cardiac resynchronization therapy pacing pulse, and wherein coupling the first capacitor to the first electrode comprises coupling the first capacitor to the first electrode for delivery of a second cardiac resynchronization therapy pacing pulse, and coupling the second capacitor to the first electrode comprises coupling the second capacitor the first electrode for delivery of a first extra-systolic pulse, and the method further comprising coupling a fourth capacitor to the second electrode for delivery of a second extra-systolic pulse.

8. A method according to claim 7, wherein coupling the second capacitor to the first electrode comprises delivering the first extra-systolic pulse at a first time and with a first amplitude, and coupling the fourth capacitor to the second electrode comprises delivering the second extra-systolic pulse at a second time and with a second amplitude.

9. A method according to claim 8, further comprising:

delivering cardiac resynchronization pacing pulses during a first period; and delivering extra-systolic pulses during a second period.

10. A method according to claim 8, wherein delivering extra-systolic pulses comprises delivering extra-systolic pulses following expiration of an extra-systolic interval after delivery of cardiac resynchronization pacing pulses.

11. An apparatus comprising:

means for coupling a first capacitor that stores energy to an electrode at a first time for delivery of a first pacing pulse to a heart; and means for coupling a second capacitor that stores energy to the electrode at a second time for delivery of a second pacing pulse to the heart, wherein the electrode is a first electrode, and means for coupling the second capacitor to a second electrode for delivery of a first cardiac resynchronization therapy pacing pulse, and wherein the means for coupling the first capacitor to the first electrode comprises means for coupling the first capacitor to the first electrode for delivery of a second cardiac resynchronization therapy pacing pulse, and the means for coupling the second capacitor to the first electrode comprises means for coupling the second capacitor to the first electrode for delivery of an extra-systolic pulse.

12. An apparatus comprising:

means for coupling a first capacitor that stores energy to an electrode at a first time for delivery of a first pacing pulse to a heart; and means for coupling a second capacitor that stores energy to the electrode at a second time for delivery of a second pacing pulse to the heart, wherein the electrode comprises a first electrode, the apparatus further comprising means for coupling a third capacitor to a second electrode for delivery of a first cardiac resynchronization therapy pacing pulse, and wherein the means for coupling the first capacitor to the first electrode comprises means for coupling the first capacitor to the first electrode for delivery of a second cardiac resynchronization therapy pacing pulse, and the means for coupling the second capacitor to the first electrode further comprises means for coupling the second capacitor the first electrode for delivery of a first extra-systolic pulse, and the apparatus further comprising means for coupling a fourth capacitor to the second electrode for delivery of a second extra-systolic pulse.

13. An apparatus according to claim 12, wherein the means for coupling the second capacitor to the first electrode comprises means for delivering the first extra-systolic pulse at a first time and with a first amplitude, and means for coupling the fourth capacitor to the second electrode further comprises means for delivering the second extra-systolic pulse at a second time and with a second amplitude.

14. An apparatus according to claim 13, further comprising:

means for delivering cardiac resynchronization pacing pulses during a first period; and means for delivering extra-systolic pulses during a second period.

15. An apparatus according to claim 13, wherein the means for delivering extra-systolic pulses comprises means for delivering extra-systolic pulses following expiration of an extra-systolic interval after delivery of cardiac resynchronization pacing pulses.

16. An apparatus according to claim 12, wherein the electrode comprises one electrode of an electrode pair and wherein said one electrode is adapted to couple to the heart in one of the following locations: an endocardial location, an epicardial location, a transvenous location, a subcutaneous location, a pericardial location, a location within a cardiac vein, a location within a coronary sinus.

* * * * *